US012558265B2

(12) United States Patent
Dennis

(10) Patent No.: US 12,558,265 B2
(45) Date of Patent: Feb. 24, 2026

(54) ENHANCED EARPLUG DEVICE WITH ADVANCED ACOUSTIC FILTERING AND SMART LIGHTING SYSTEM

(71) Applicant: John Maxwell Norman Dennis, Denver, CO (US)

(72) Inventor: John Maxwell Norman Dennis, Denver, CO (US)

( * ) Notice: Subject to any disclaimer, the term of this patent is extended or adjusted under 35 U.S.C. 154(b) by 0 days.

(21) Appl. No.: 19/260,716

(22) Filed: Jul. 7, 2025

(65) Prior Publication Data

US 2025/0332033 A1     Oct. 30, 2025

Related U.S. Application Data

(63) Continuation of application No. 17/889,448, filed on Aug. 17, 2022, now abandoned.

(60) Provisional application No. 63/234,434, filed on Aug. 18, 2021.

(51) Int. Cl.
| | |
|---|---|
| *A61F 11/08* | (2006.01) |
| *F21S 9/02* | (2006.01) |
| *F21V 33/00* | (2006.01) |
| *F21Y 115/10* | (2016.01) |

(52) U.S. Cl.
CPC ................. *A61F 11/08* (2013.01); *F21S 9/02* (2013.01); *F21V 33/0064* (2013.01); *A61F 2250/0097* (2013.01); *F21Y 2115/10* (2016.08)

(58) Field of Classification Search
CPC .......... A61F 11/08; A61F 11/12; A61F 11/14; A61F 11/06; A61F 2250/0097; F21S 9/02; F21V 33/0064; F21Y 2115/10
See application file for complete search history.

(56) References Cited

U.S. PATENT DOCUMENTS

| | | | | |
|---|---|---|---|---|
| 9,491,533 | B2 * | 11/2016 | Matsuo ................. | H04R 1/1016 |
| 2015/0304761 | A1 * | 10/2015 | Montazemi .......... | H04R 1/1083 |
| | | | | 381/72 |
| 2018/0338688 | A1 * | 11/2018 | Kashiwase ........... | A61B 5/0261 |
| 2020/0188176 | A1 * | 6/2020 | Cran .................... | G10K 11/162 |
| 2023/0053448 | A1 * | 2/2023 | Dennis .................. | A61F 11/08 |

(Continued)

OTHER PUBLICATIONS

Xu et al., CN 203120121 "Can Change Light Flicker with Audio Earphone Device" (Year: 2013).*

(Continued)

*Primary Examiner* — Mong-Thuy T Tran
(74) *Attorney, Agent, or Firm* — Schell IP

(57) ABSTRACT

An enhanced earplug device for noise suppression and entertainment lighting comprises a tubular housing with a removable tip portion for ear canal insertion and a visible light element. The device incorporates a quartz acoustic filter for high-fidelity sound preservation while reducing volume, and a vibration sensor detecting musical beats in the 20-250 Hz range for music-reactive lighting patterns. Bluetooth connectivity enables inter-device synchronization and mobile app control. A tap sensor integrated into the housing exterior provides intuitive gesture-based mode switching between static color, music-reactive, and synchronized operational modes. The system includes RF capabilities for professional venue integration via centralized controllers with DMX/MIDI connectivity, enabling coordinated lighting displays across multiple users in entertainment environments.

25 Claims, 6 Drawing Sheets

(56) References Cited

U.S. PATENT DOCUMENTS

| | | | |
|---|---|---|---|
| 2023/0066293 A1* | 3/2023 | Lee ...................... | H04R 1/1008 |
| 2023/0269513 A1* | 8/2023 | Cousins .............. | H04R 1/1075 |
| | | | 381/171 |

OTHER PUBLICATIONS

Liao et al., WO 2018191905 "Light Emitting Earphone" (Year: 2018).*
Wei, CN 216134577, "Wireless Earphone" (Year: 2021).*
Zhang, CN 105142062 "Passive Luminous Earphone" (Year: 2015).*

* cited by examiner

ENHANCED EARPLUG DEVICE WITH ADVANCED ACOUSTIC FILTERING AND SMART LIGHTING SYSTEM

CROSS REFERENCE TO RELATED APPLICATIONS

This application is a continuation-in-part of U.S. patent application Ser. No. 17/889,448, filed Aug. 17, 2022, which claims priority to U.S. Provisional Patent Application No. 63/234,434, filed Aug. 18, 2021, both of which are incorporated herein by reference in their entirety.

FIELD OF THE INVENTION

The present invention relates to enhanced earplug devices configured for noise suppression while providing advanced lighting capabilities and smart connectivity features. More particularly, the invention relates to noise cancelling earplugs that address fundamental problems in existing earplug technology including poor acoustic performance, unappealing aesthetics, comfort issues, and lack of interactive features for entertainment environments.

BACKGROUND OF THE INVENTION

Current earplug technology suffers from several significant limitations that discourage widespread adoption and limit effectiveness in various applications. Traditional earplugs, particularly foam-based designs, create substantial problems that the present invention seeks to address.

A primary limitation of existing earplugs is their failure to preserve sound quality while reducing volume. People typically avoid wearing earplugs because conventional designs diminish both the clarity and volume of sound, creating a "muddy" audio experience that makes speech and music difficult to understand. Traditional earplugs have not evolved significantly over time, continuing to use thermoplastic filters or basic foam materials that degrade audio fidelity rather than preserving the high-frequency components essential for clear sound reproduction.

The aesthetics of conventional foam earplugs present significant barriers to adoption. Users, particularly in social settings such as concerts, experience embarrassment when wearing traditional earplugs due to their unattractive appearance. The foam earplugs currently available have remained largely unchanged in design and appearance, failing to meet the aesthetic expectations of users in entertainment environments where visual presentation is important.

Existing earplug designs often cause discomfort during extended wear, further discouraging consistent use when hearing protection is most needed. Poor ergonomic design and limited customization options result in inadequate sealing or excessive pressure within the ear canal.

Current earplugs provide no visual indication of proper placement or use, creating safety concerns in work environments where supervisors need to verify that workers are wearing appropriate hearing protection. The absence of any visibility features makes it difficult to confirm compliance with safety regulations or to locate earplugs in low-light conditions.

In entertainment venues, particularly in the electronic dance music (EDM) scene, there exists an unmet need for hearing protection that integrates with the visual entertainment experience. Current earplugs fail to provide any interactive or aesthetic features that would enhance rather than detract from the entertainment experience. Users desire products that can participate in the lighting and visual effects that are central to modern entertainment venues.

Existing earplugs lack user control mechanisms for adjusting performance characteristics based on different acoustic environments. Users cannot modify the behavior of their hearing protection to adapt to varying noise levels, music types, or personal preferences without physically replacing the devices. Some electronic earplugs additionally require cumbersome battery management and lack modern connectivity features that would enable coordinated operation between paired devices or integration with venue-wide systems.

Current earplug designs fail to incorporate modern sensor technology, wireless communication capabilities, or interactive control systems that could significantly enhance both functionality and user experience. The absence of features such as beat detection, music synchronization, and touch-sensitive controls represents a significant gap in available technology.

Traditional acoustic filtering materials, particularly thermoplastic filters, lack the density characteristics necessary for maintaining sound wave stability while providing effective noise reduction. There exists a need for advanced filtering materials that can reduce volume without compromising audio clarity or frequency response.

Accordingly, there is a substantial need for an enhanced earplug system that addresses these fundamental limitations while providing advanced features suitable for both safety applications and entertainment environments. The present invention seeks to solve these problems through innovative acoustic filtering, aesthetic enhancement, smart connectivity, and user control capabilities that represent significant advances over existing earplug technology.

SUMMARY OF THE INVENTION

Exemplary embodiments of the present invention provide a comprehensive solution to the fundamental limitations of existing earplug technology by combining advanced acoustic filtering, sophisticated lighting capabilities, smart connectivity features, and intuitive user controls in a unified earplug system designed for both hearing protection and entertainment enhancement.

In an embodiment of the invention, an enhanced earplug device comprises a generally tubular housing having a first end with a removable tip portion configured for ear canal insertion and a second end with a visible light element. The embodiment incorporates a quartz acoustic filter positioned adjacent to the first end within the housing interior space, providing superior sound quality preservation while reducing volume through the unique density advantages of quartz material for maintaining sound wave stability. An exemplary embodiment includes a vibration sensor configured to detect musical beats in a frequency range of 20 Hz to 250 Hz, enabling music-reactive lighting patterns that synchronize with detected audio rhythms.

An embodiment includes Bluetooth connectivity for inter-device synchronization between paired earplugs and mobile device communication for comprehensive user control through smartphone applications. The exemplary embodiment incorporates tap sensor technology integrated into the exterior housing surface, enabling intuitive gesture-based control for mode switching, color changes, and brightness adjustment through single taps, double taps, and long press gestures.

In an exemplary embodiment, the system provides multiple operational modes including static color display, music-reactive "beat synch" mode, and synchronized group operation. The embodiment includes power management systems comprising lithium batteries within each earplug and a rechargeable charging case with USB-C connectivity.

An embodiment of the invention incorporates mobile application control systems that enable users to adjust lighting parameters, manage device pairing, and coordinate multiple earplug sets simultaneously through smartphone interfaces. The exemplary embodiment includes group management capabilities allowing one user to control lighting settings for entire groups of wearers, creating synchronized visual experiences across multiple participants.

In an embodiment, the system includes professional venue integration through centralized RF control systems comprising main controller units that interface with existing DJ equipment and concert sound mixing boards. The exemplary embodiment incorporates DMX and MIDI interface capabilities for direct integration with professional lighting consoles and DJ performance controllers, enabling coordinated audio-visual performances and full-scale show integration.

An embodiment provides real-time beat detection algorithms that analyze incoming audio signals to generate corresponding light pattern commands, with automatic gain control and adaptive synchronization logic that maintains precise timing between detected beats and light output. The exemplary embodiment includes venue mapping capabilities and zone designation protocols that enable selective control of different earplug groups based on physical location within entertainment venues.

Embodiments of the invention address the core problems of traditional earplugs including poor sound quality degradation, unappealing aesthetics, comfort issues, and lack of interactive features, particularly in entertainment environments where coordinated visual displays enhance the user experience. The invention is particularly suited for EDM scenes, concerts, and professional entertainment venues where hearing protection and visual participation are both desired.

In exemplary embodiments, the enhanced earplug system provides passive acoustic filtering without requiring electronics for sound reduction, while simultaneously offering sophisticated smart lighting capabilities that integrate with modern entertainment technology infrastructure. The embodiments demonstrate significant advances over existing earplug technology through the integration of advanced materials, sensor technology, wireless communications, and professional venue compatibility.

DETAILED DESCRIPTION

Exemplary embodiments of the present invention relate to enhanced earplugs configured to reduce noise while providing advanced lighting capabilities and smart connectivity features. More particularly, embodiments of the invention described herein relate to a noise cancelling earplug configured for receipt in an ear canal for suppressing sound while including sophisticated light elements, acoustic filtering systems, and interactive control mechanisms designed for high-fidelity acoustic performance and visual indication in entertainment environments.

Figure 1:
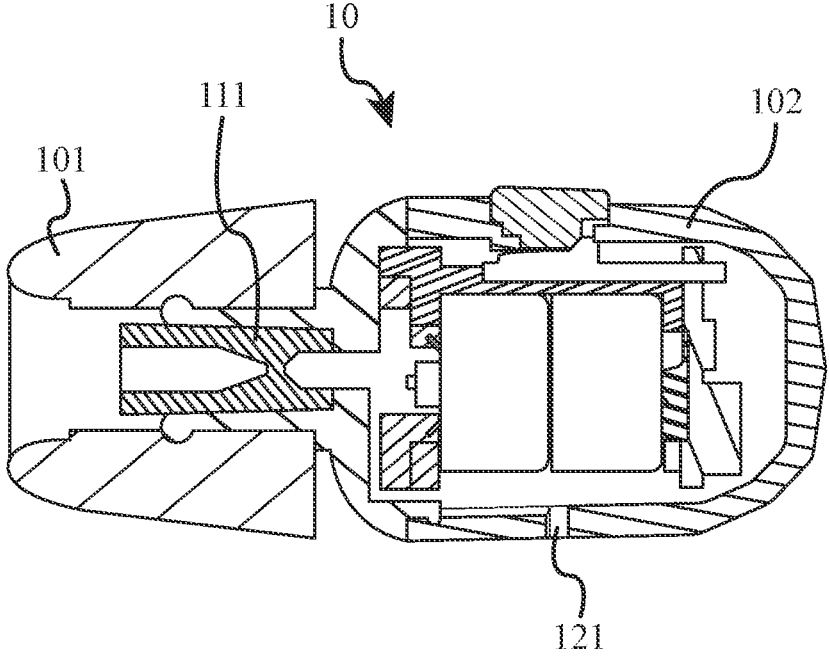
FIG. 1 is a side view of the earplug device showing housing components, light element, and structural details including vent specifications in accordance with an embodiment.

FIG. 1 illustrates a side view of the enhanced earplug device 10 in accordance with an exemplary embodiment of the present invention, showing the primary structural components and their spatial relationships. The device 10 comprises a generally tubular housing having a first end 101 and a second end 102 positioned opposite to the first end. The first end 101 is specifically configured for insertion within an ear canal and includes a removable tip portion 110 that provides anatomical compatibility with various ear canal sizes and shapes. The acoustic filter 111 is strategically positioned adjacent to the first end 101 within the housing interior space, providing the sophisticated quartz-based sound filtering capabilities that distinguish this invention from conventional earplug technology. The second end 102 features the light element 120 positioned for optimal visibility when the device is worn, ensuring that the illumination function serves both aesthetic and safety indication purposes. Critical to the acoustic performance of the device, the vent specifications are precisely engineered with a width of 0.5 mm and a depth of 0.3 mm, providing optimal pressure equalization while maintaining the integrity of the noise suppression capabilities. Additionally, a strategically positioned hole with a diameter of 0.8 mm (aperture 121) facilitates the acoustic pathway necessary for the proper functioning of the quartz acoustic filter 111, allowing controlled sound transmission through the device while preserving the high-fidelity audio characteristics that represent a significant advancement over traditional foam earplug technology.

Figure 2:
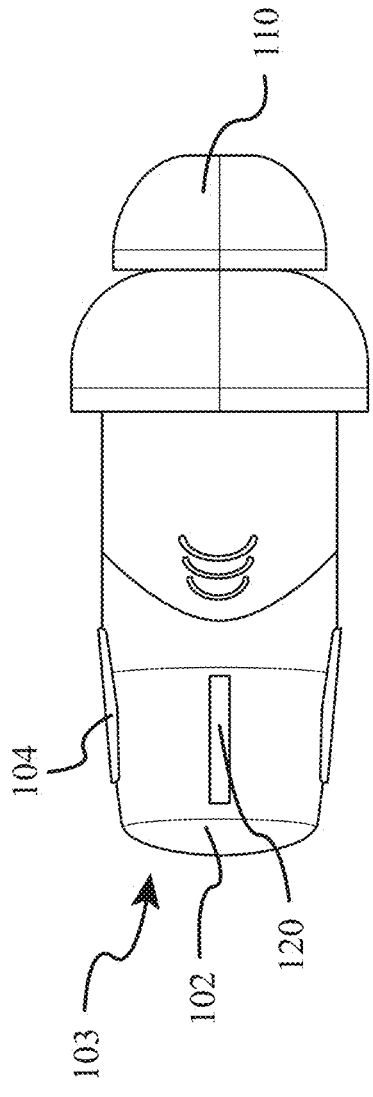
FIG. 2 is a cross-sectional view showing internal components including power source, switch, and housing structure in accordance with an embodiment.

FIG. 2 provides a detailed cross-sectional view of the enhanced earplug device 10, revealing the sophisticated internal architecture and electronic components that enable the advanced functionality described in this invention. The internal cavity of the housing 100 accommodates the power source 103, which in preferred embodiments comprises either a Zinc-air battery or an AG2 battery configuration optimized for the compact form factor requirements of the earplug design. The switch 104 is strategically positioned within the housing structure to provide user-accessible control over the light element 120 operation while maintaining the ergonomic integrity of the device. The housing structure 110 provides the foundational framework that supports all internal components while ensuring proper spacing and isolation between the acoustic and electronic systems. The light element 120 is positioned at the second end 102 in optimal alignment for maximum visibility and light transmission through the translucent housing material, enabling the distinctive lighting capabilities that form a core aspect of the inventive concept. The cross-sectional perspective reveals how the various components are integrated within the compact tubular form factor, demonstrating the sophisticated engineering required to combine traditional earplug functionality with advanced electronic lighting systems, Bluetooth connectivity, and sensor technology while maintaining the comfortable fit and effective noise suppression characteristics essential for user acceptance in entertainment environments.

Figure 3:
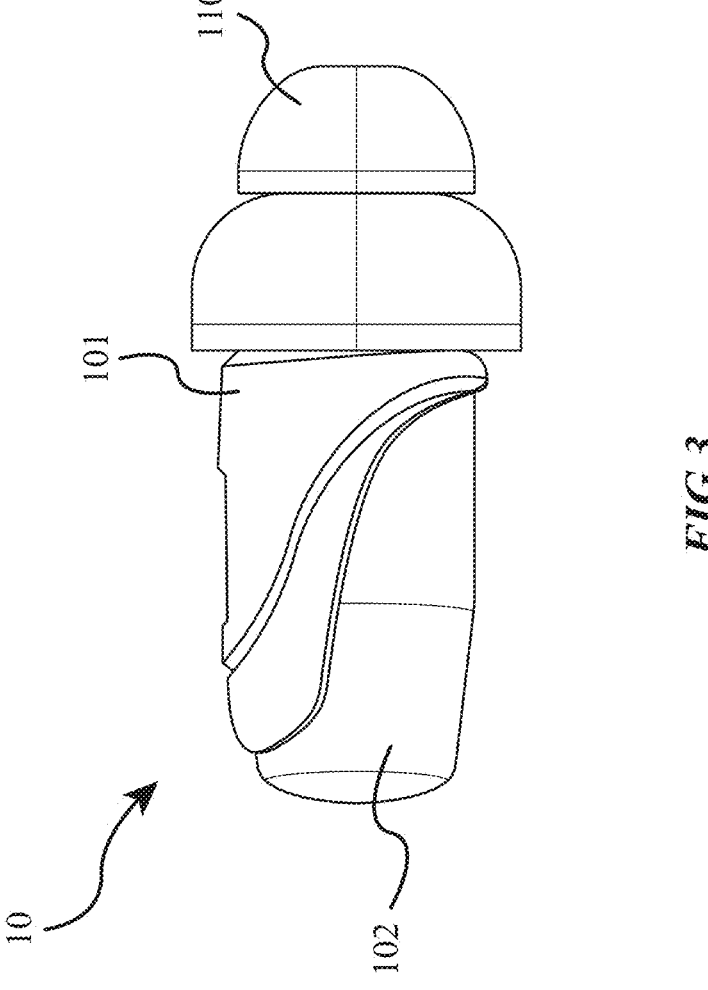
FIG. 3 illustrates dimensional specifications and battery configurations including Zinc-air and AG2 battery options in accordance with an embodiment.

FIG. 3 depicts the dimensional specifications and battery configuration options that demonstrate the practical implementation considerations for the enhanced earplug device 10. The figure illustrates the precise dimensional requirements, including the overall length measurement of 0.32 units and the critical diameter specification of 10.21 units that ensure proper fit within standard ear canal dimensions while accommodating the internal electronic components. The battery configuration options are comprehensively shown, featuring both the #10 Zinc-air battery and the AG2 battery alternatives, each selected for their optimal power-to-size ratio and their ability to provide sustained operation for the LED lighting systems and Bluetooth connectivity functions. The dimensional specifications reflect careful ergonomic analysis to ensure that the device 10 maintains comfortable wearability during extended use periods while providing sufficient internal volume for the power source 103, electronic circuitry, acoustic filter 111, and light element 120. The figure demonstrates how the various components, including the first end 101, second end 102, and tip portion 110, are proportioned to achieve the optimal balance between acoustic performance, electronic functionality, and user comfort. These specifications represent critical design parameters that enable the device to function effectively in the demanding environment of entertainment venues where both hearing protection and visual display capabilities are essential for user satisfaction and safety compliance.

Figure 4:
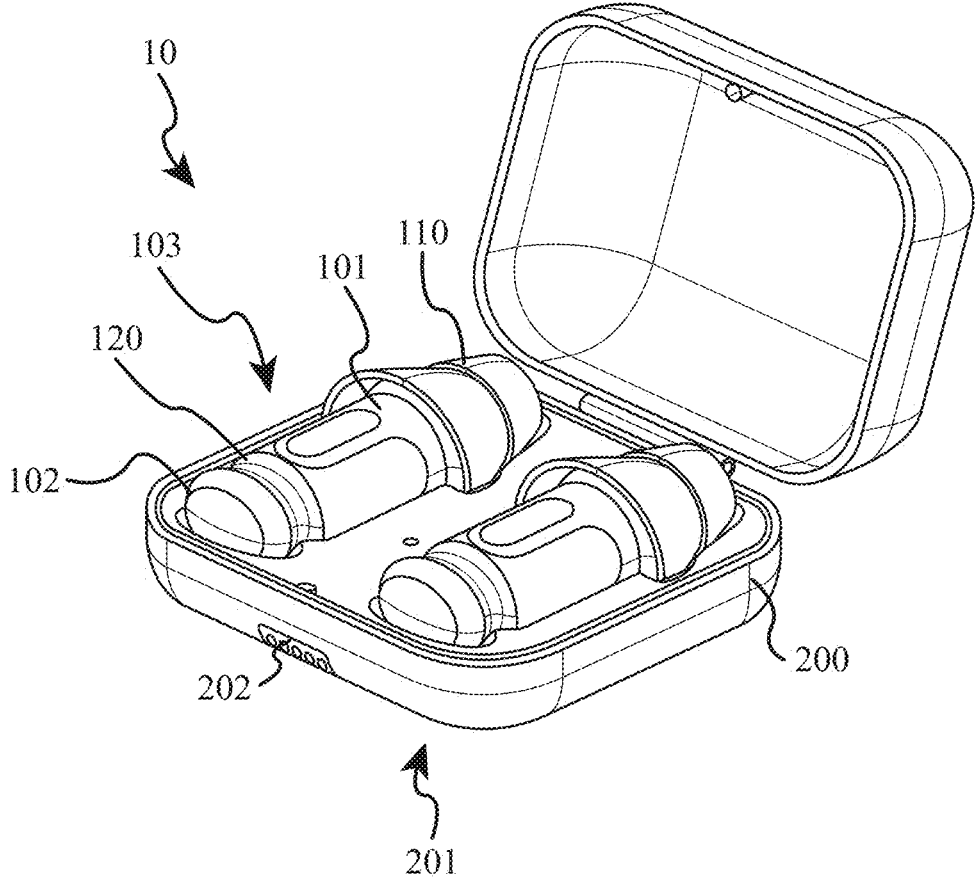
FIG. 4 depicts alternative embodiment views showing paired device configuration for left and right earplugs in accordance with an embodiment.

FIG. 4 illustrates alternative embodiment configurations of the enhanced earplug system, specifically highlighting the paired device implementation that represents a significant advancement in coordinated earplug technology. The figure shows two complete earplug devices 10 configured for left and right ear operation, each incorporating the essential components including the tip portion 110, first end 101, power source 103, light element 120, and second end 102. The charging case configuration is prominently featured, showing the case 200 with integrated charging contacts 202 and the secondary power source 2001 that enables convenient recharging of the individual earplug power sources 103. This embodiment demonstrates the sophisticated power management system that eliminates the inconvenience of disposable batteries while providing extended operational capability for the advanced electronic features. The paired configuration enables the synchronized lighting operations that are central to the entertainment applications of the invention, allowing coordinated visual displays between the left and right earplugs through the integrated Bluetooth communication systems. The charging case 200 not only provides power management functionality but also serves as a protective storage solution, ensuring that the delicate electronic components are properly maintained when not in use. The charging contacts 202 are positioned for optimal electrical connection with corresponding contacts on the earplug housings, enabling efficient power transfer while maintaining the water-resistant properties necessary for reliable operation in various environmental conditions typical of entertainment venues.

Figure 5:
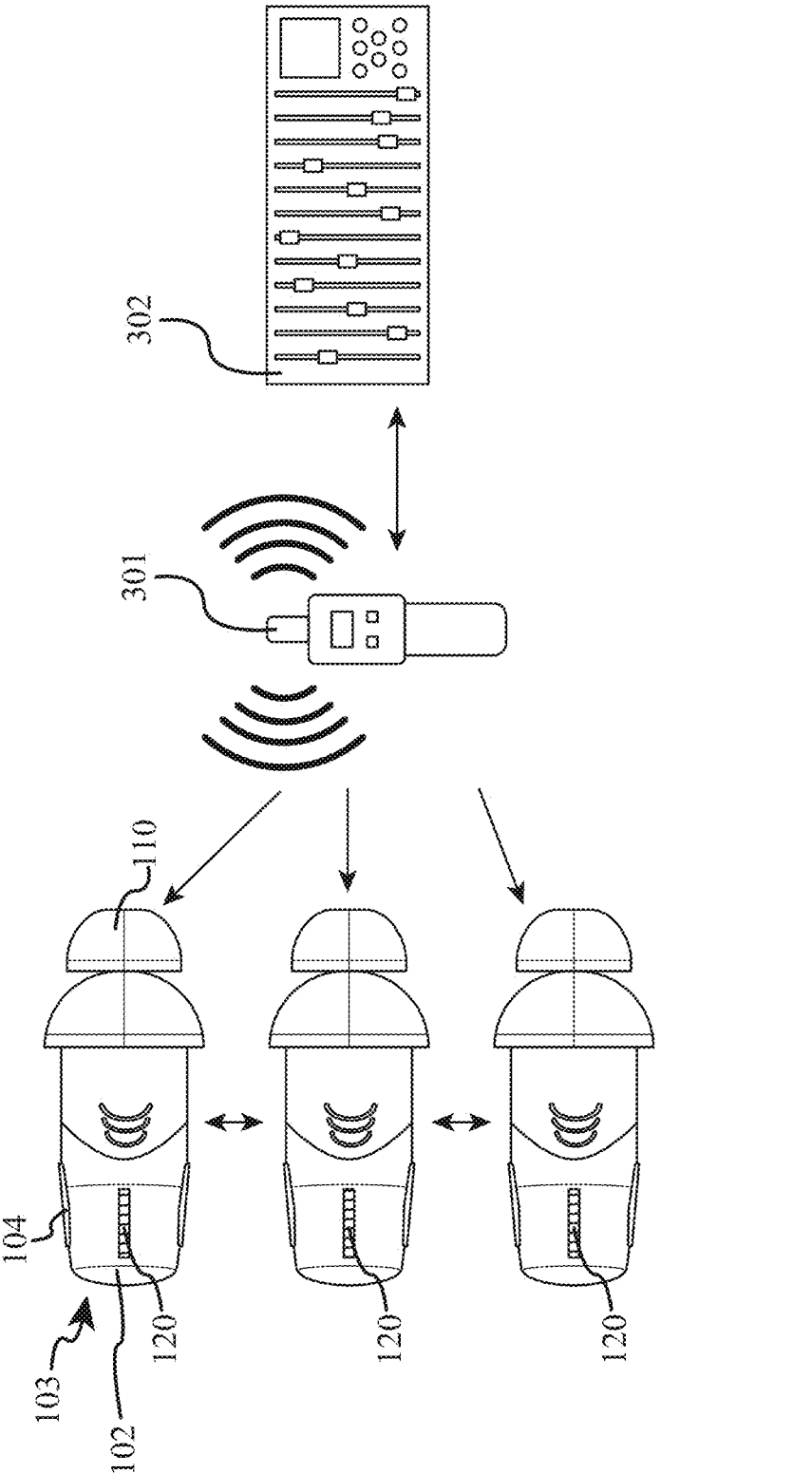
FIG. 5 shows professional venue integration components including RF remote (301) and MIDI/DMX board for centralized control systems in accordance with an embodiment.

FIG. 5 demonstrates the professional venue integration capabilities that distinguish this invention as a comprehensive solution for large-scale entertainment applications. The figure prominently features the RF remote control unit 301 and the MIDI/DMX interface board 302, which together provide the technological infrastructure necessary for coordinated lighting control across multiple earplug devices within entertainment venues. The RF remote 301 enables centralized wireless control of lighting effects, allowing venue operators or event coordinators to synchronize lighting displays across entire audiences wearing the enhanced earplugs. The MIDI/DMX board 302 provides professional-grade integration with existing entertainment industry control systems, enabling direct connection to lighting consoles, DJ equipment, and professional audio systems commonly found in concert venues, nightclubs, and festival environments. The device 10 components, including the light element 120, are shown in the context of this professional integration system, demonstrating how individual earplugs can participate in large-scale coordinated lighting displays that enhance the overall entertainment experience. This professional venue integration represents a significant departure from traditional earplug applications, transforming hearing protection devices into active participants in the visual entertainment experience while maintaining their core function of protecting user hearing in high-volume environments.

Figure 6:
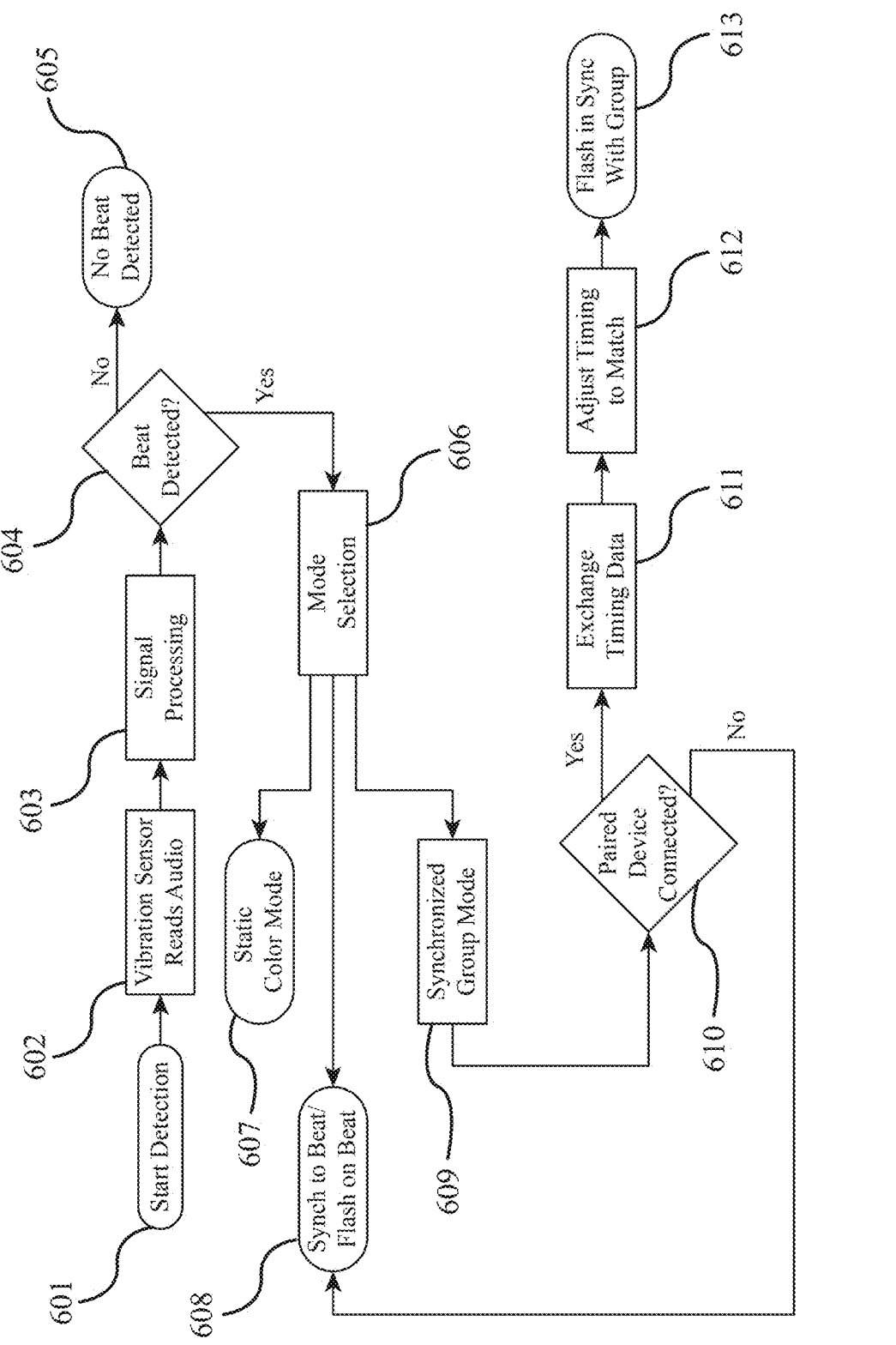
FIG. 6 is a flowchart illustrating vibration sensor operation, beat detection algorithms, and mode selection logic for music-reactive lighting patterns in accordance with an embodiment.

FIG. 6 presents a flowchart illustrating the sophisticated beat detection algorithms and mode selection logic that enable the music-reactive lighting capabilities central to the inventive concept in accordance with an embodiment. The flowchart begins with the vibration sensor operation (601) where the system continuously monitors environmental audio through the integrated piezoelectric accelerometer calibrated for the 20 Hz to 250 Hz frequency range characteristic of musical bass and percussive elements. The signal processing stage (602) implements frequency-selective filtering and automatic gain control to isolate musical beat components from background noise and environmental vibrations. The beat detection decision point (603) utilizes advanced algorithms to determine whether valid musical beats are present in the processed signal. When no beat is detected (604), the system defaults to static color mode operation (607), providing consistent illumination that serves the safety and aesthetic functions of the device. Upon successful beat detection (605), the system activates the synchronized beat-matching mode (608) where the LED lighting patterns correspond directly to the detected musical rhythm. The mode selection logic (609) enables users to choose between various operational states including static color display, music-reactive patterns, and synchronized group operation. The paired device connectivity assessment (610) determines whether Bluetooth communication with a paired earplug is active, enabling coordinated lighting effects between left and right devices. The timing data exchange (611) and timing adjustment (612) functions ensure precise synchronization between paired devices, maintaining visual coherence even when ambient audio conditions differ between ear positions. Finally, the synchronized group flash operation (613) coordinates lighting patterns across multiple paired devices, creating unified visual displays that enhance the entertainment experience while preserving the individualized hearing protection that remains the fundamental purpose of the earplug system.

In an exemplary embodiment, the invention addresses several technical problems not solved by existing earplug technology. Traditional earplugs suffer from significant limitations including poor sound quality degradation, uncomfortable fit, and unappealing aesthetics that discourage use. An embodiment of the invention recognizes that people typically avoid wearing earplugs because existing designs diminish both clarity and volume of sound, creating a "muddy" audio experience.

Exemplary embodiments of the present invention further address the aesthetic limitations of conventional foam earplugs, which create embarrassment for users in social settings such as concerts due to their unattractive appearance. The invention also solves comfort issues associated with traditional earplug designs.

An exemplary embodiment of the enhanced earplug device comprises a housing 100 that is generally tubular in shape and includes a first end 101 and a second end 102. In this embodiment, the first end 101 includes a removable tip portion 110 configured for receipt within various sizes and anatomical shapes of ear canals. The exemplary embodiment includes a light element 120 positioned at the second end 102 for visibility and illumination.

In an embodiment of the invention, the device 10 includes a power source 103 coupled to the light source 120 for selectively illuminating the light source. The preferred embodiment utilizes a button-style battery, such as a Zinc-air battery, in coupling with a light emitting diode (LED) positioned on the second end of each earplug.

A key embodiment of the invention incorporates a quartz acoustic filter positioned adjacent to the first end within the housing interior space. This exemplary embodiment provides high-fidelity sound preservation while reducing volume, representing a significant advancement over traditional thermoplastic filters.

In the exemplary embodiment, the quartz acoustic filter offers unique density advantages for maintaining sound wave stability, resulting in superior audio quality compared to conventional earplugs that produce "muddy" sound. The embodiment provides passive noise filtering without requiring electronics for the sound reduction functionality.

An embodiment of the invention includes the acoustic filter 111 in communication with a pathway within the interior space through an aperture 121 in the second end 102, wherein noise is directed through the aperture 121 and the filter 111 before reaching the interior ear of a wearer. In this embodiment, the filter may be modified or selected to combat certain types or decibel levels of a given noise.

An exemplary embodiment of the invention incorporates Bluetooth connectivity for inter-ear synchronization of lighting effects. This embodiment includes a vibration sensor positioned within the housing for detecting low-frequency audio signals, enabling the system to adapt light patterns based on detected music or audio input. An exemplary embodiment incorporates a Bluetooth communication module comprising a low-energy Bluetooth 5.0 transceiver positioned within the housing interior space and configured to establish bidirectional wireless communication with a corresponding Bluetooth module in a paired earplug device. The embodiment includes device pairing protocols that enable automatic recognition and connection between left and right earplug devices through unique device identifier exchange and authentication handshaking procedures. In the exemplary embodiment, the Bluetooth communication module implements real-time synchronization algorithms that coordinate lighting state changes between paired devices with latency compensation of less than 10 milliseconds to ensure visually synchronized lighting effects.

The embodiment provides lighting state synchronization protocols wherein changes to lighting mode, color selection, or brightness level on one earplug device automatically trigger corresponding state update commands transmitted via Bluetooth to the paired device. An exemplary embodiment includes master-slave communication architecture where the first device to detect user input becomes the temporary master and broadcasts lighting commands to the slave device, with automatic role switching capability to maintain synchronized operation regardless of which device receives user input. The embodiment incorporates synchronized beat detection sharing where musical rhythm patterns detected by the vibration sensor in one earplug are transmitted to the paired device to ensure coordinated music-reactive lighting patterns even when ambient vibration levels differ between the left and right ear positions.

The exemplary embodiment includes music-reactive light patterns that operate in a "beat synch" mode, allowing the earplugs to flash or change color in synchronization with detected audio frequencies. An embodiment also incorporates a tap sensor comprising a small sensitive filament positioned on the exterior shell, enabling mode switching and color changes when the earplug surface is tapped.

In an exemplary embodiment, the system provides multiple operational modes including static color display, music-reactive patterns, and synchronized operation between paired earplugs. The embodiment is particularly designed for use in EDM scenes and entertainment environments where visual display elements are desired.

An exemplary embodiment incorporates a multi-part housing construction comprising discrete upper and lower housing components for both left and right earplug devices. The left upper housing and right upper housing form the primary structural framework for the left and right earplugs respectively, each incorporating mounting points for the LED elements and providing the exterior surface finish including spray painting and screen printing for aesthetic enhancement. The let lower housing and right lower housing provide the foundation structure for electronic component integration, including dedicated mounting areas for PCBA circuit boards, battery compartments, and sensor positioning. The multi-part housing design enables efficient manufacturing assembly while maintaining precise tolerances for acoustic sealing and electronic component protection.

An embodiment includes specialized LED case components comprising a left LED case and a right LED case that provide dedicated mounting structures for the light elements within each earplug housing. These LED cases are positioned within the translucent case component that forms the light-transmissive portion of the housing structure, enabling optimal light output while maintaining the structural integrity of the device. The translucent case material is specifically selected for maximum light transmission efficiency while providing adequate protection for the internal LED components and associated circuitry.

An embodiment of the invention includes a lithium battery positioned within each earplug housing to power the lighting elements. The exemplary embodiment incorporates a rechargeable case with USB-C charging capability for convenient power management.

An embodiment includes RF linkage capabilities to connect with centralized controllers for venue-wide synchronization of light pulses, particularly suited for concert or club environments. This embodiment enables coordinated lighting displays across multiple users in entertainment venues. An exemplary embodiment incorporates a vibration sensor assembly positioned within the housing interior space adjacent to the acoustic filter, wherein the vibration sensor comprises a piezoelectric accelerometer specifically calibrated to detect low-frequency vibrations in the range of 20 Hz to 250 Hz corresponding to musical bass frequencies and percussive elements. The embodiment includes a three-axis MEMS accelerometer with integrated signal conditioning circuitry capable of detecting mechanical vibrations transmitted through the housing material from external audio sources.

In an exemplary embodiment, the vibration sensor assembly includes frequency-selective filtering circuitry that isolates musical beat components by implementing high-pass and low-pass filter stages with cutoff frequencies specifically tuned to emphasize rhythmic elements between 60 Hz and 150 Hz. The embodiment incorporates automatic gain control algorithms that adjust sensor sensitivity based on ambient vibration levels to maintain consistent beat detection performance across varying environmental conditions.

An exemplary embodiment incorporates a metal rotating shaft and spring mechanism that enable the removable tip functionality described herein. The metal rotating shaft provides a durable rotation interface between the tip portion 110 and the main housing structure, enabling users to easily replace or adjust tip components for optimal ear canal fit. The spring mechanism provides controlled tension for the rotating shaft operation while maintaining proper sealing characteristics when the tip portion is engaged. This mechanical assembly ensures reliable operation through repeated use cycles while preserving the acoustic isolation properties essential for effective noise suppression.

The embodiment includes beat detection algorithms comprising peak detection circuitry that analyzes the filtered vibration signal to identify rhythmic patterns characteristic of musical beats. An exemplary embodiment implements tempo tracking algorithms that calculate beats-per-minute (BPM) in real-time by measuring time intervals between detected vibration peaks, with BPM detection ranging from 60 to 180 beats per minute to accommodate various musical genres.

An embodiment of the invention incorporates alternative audio input methods including a miniature omnidirectional microphone element positioned within the housing near the second end 102, wherein the microphone comprises a MEMS microphone with integrated analog-to-digital conversion capabilities. The exemplary embodiment includes acoustic coupling structures that enable the microphone to detect external audio signals while maintaining the acoustic sealing properties of the earplug.

In an exemplary embodiment, the microphone-based system includes digital signal processing algorithms that perform fast Fourier transform (FFT) analysis on incoming audio signals to identify frequency components characteristic of musical beats and rhythm sections. The embodiment incorporates onset detection algorithms that analyze spectral flux and energy variations in the audio signal to precisely identify the timing of musical beats and percussive events.

The embodiment provides light synchronization protocols wherein detected beat timing information triggers pre-programmed light patterns stored in non-volatile memory within the device. An exemplary embodiment includes beat-to-light mapping algorithms that translate detected BPM values into corresponding flash rates, with options for 1:1 beat matching, half-time patterns, and double-time patterns based on user preferences.

An embodiment incorporates adaptive synchronization logic that automatically adjusts light pattern timing based on beat prediction algorithms that anticipate upcoming beats based on established tempo patterns. The exemplary embodiment includes phase-locked loop circuitry that maintains precise synchronization between detected audio beats and light output timing, with compensation for processing delays to ensure visual-audio alignment.

In an exemplary embodiment, the system provides multiple beat synchronization modes including bass-reactive mode that responds primarily to low-frequency drum and bass elements, full-spectrum mode that reacts to all musical elements, and percussion-only mode that specifically targets drum beats and percussive instruments. The embodiment includes sensitivity adjustment controls accessible through tap gesture sequences that enable users to customize beat detection thresholds for different musical styles and volume levels.

The embodiment incorporates anti-false trigger mechanisms including minimum beat interval timers and signal validation algorithms that prevent erroneous light activation from non-musical vibrations such as movement, handling, or environmental noise. An exemplary embodiment includes adaptive filtering that learns to distinguish between intentional musical input and incidental vibrations through pattern recognition algorithms.

The preferred embodiment comprises a device 10 that is generally tubular in shape with a housing 100 defining an interior space and comprising a first end 101 and a second end 102. In this embodiment, the distance between the first end 101 and second end 102 defines the length of the device 10, which is selected to position the second end exterior to the ear canal for light element visibility.

An exemplary embodiment includes a removable tip portion 110 at the first end 101 that creates a seal between the device 10 and the ear canal to suppress noise. The embodiment provides capabilities to receive several sizes and shapes of tips to accommodate various ear canal configurations. In the preferred embodiment, the tip portion 110 is constructed of resilient material such as rubbers, silicones, or similar materials.

An exemplary embodiment positions the quartz acoustic filter within the housing interior space adjacent to the first end. This embodiment provides superior acoustic performance characteristics and frequency response compared to traditional thermoplastic filters due to the enhanced density properties of quartz material.

In an embodiment of the invention, the acoustic filter system includes installation and replaceability features for the quartz filter elements, enabling user customization and maintenance. The embodiment maintains the passive filtering approach without requiring electronic components for the acoustic function.

The exemplary embodiment incorporates LED light sources within the housing 100 that may be comprised of transparent or translucent material to allow light transmission from the interior to the exterior at the second end 102. An advanced embodiment includes Bluetooth module placement and antenna configuration for wireless connectivity.

The embodiment includes vibration sensor positioning for optimal frequency detection within the housing structure. An exemplary embodiment integrates the tap sensor into the housing exterior surface to enable intuitive user control.

In a preferred embodiment, the light element 120 is a light emitting diode with the ability to change into a plurality of colors selected by a user during operation. The embodiment may include design elements such as illuminated logos, slogans, shapes, messages, monograms, or other similar designs.

An embodiment of the invention incorporates music reactive algorithms for beat detection and light synchronization with detected audio patterns. The exemplary embodiment includes mode switching logic via tap sensor interface, enabling users to cycle between static color, music-reactive, and synchronized operational modes.

An exemplary embodiment incorporates a mobile application control system comprising a smartphone application interface that enables direct control of lighting modes, color preferences, and synchronization settings through wireless communication with the earplug devices. The embodiment includes Bluetooth communication protocols between mobile devices and earplug systems, allowing users to adjust lighting parameters in real-time through intuitive mobile interface controls.

In an exemplary embodiment, the mobile application provides comprehensive mode switching capabilities enabling users to select between static color modes, music-reactive patterns, and synchronized operational states through graphical user interface elements. The embodiment incorporates color customization algorithms that allow users to select specific colors, adjust brightness levels, and create custom lighting sequences through the mobile application interface.

An embodiment includes electronic integration through PCBA-1 and PCBA-2 circuit board assemblies that provide the foundation for all electronic functionality described herein. PCBA-1 serves as the main controller board integrating the Bluetooth communication modules, vibration sensor interfaces, and power management circuitry within the charging case assembly. PCBA-2 comprises the individual earplug circuit boards, with two units required for left and right earplug operation, each incorporating LED driver circuits, tap sensor interfaces, and wireless communication transceivers. These circuit board assemblies are specifically designed for the compact form factor requirements while providing reliable electrical connections for all system components.

An exemplary embodiment incorporates dual battery configuration comprising a first Battery A positioned within charging case for primary power storage and second Battery B component, with two units providing individual power for left and right earplug devices. The battery configuration enables extended operational periods while maintaining the compact form factor essential for comfortable earplug wear. The charging case battery provides sufficient capacity for multiple charging cycles of the individual earplug batteries, ensuring continuous availability for extended entertainment events.

An exemplary embodiment incorporates a vibration sensor assembly positioned within the housing interior space adjacent to the acoustic filter, wherein the vibration sensor comprises a piezoelectric accelerometer specifically calibrated to detect low-frequency vibrations in the range of 20 Hz to 250 Hz corresponding to musical bass frequencies and percussive elements. The embodiment includes a three-axis MEMS accelerometer with integrated signal conditioning circuitry capable of detecting mechanical vibrations transmitted through the housing material from external audio sources.

In an exemplary embodiment, the vibration sensor assembly includes frequency-selective filtering circuitry that isolates musical beat components by implementing high-pass and low-pass filter stages with cutoff frequencies specifically tuned to emphasize rhythmic elements between 60 Hz and 150 Hz. The embodiment incorporates automatic gain control algorithms that adjust sensor sensitivity based on ambient vibration levels to maintain consistent beat detection performance across varying environmental conditions.

The embodiment includes beat detection algorithms comprising peak detection circuitry that analyzes the filtered vibration signal to identify rhythmic patterns characteristic of musical beats. An exemplary embodiment implements tempo tracking algorithms that calculate beats-per-minute (BPM) in real-time by measuring time intervals between detected vibration peaks, with BPM detection ranging from 60 to 180 beats per minute to accommodate various musical genres.

An embodiment of the invention incorporates alternative audio input methods including a miniature omnidirectional microphone element positioned within the housing near the second end 102, wherein the microphone comprises a MEMS microphone with integrated analog-to-digital conversion capabilities. The exemplary embodiment includes acoustic coupling structures that enable the microphone to detect external audio signals while maintaining the acoustic sealing properties of the earplug.

In an exemplary embodiment, the microphone-based system includes digital signal processing algorithms that perform fast Fourier transform (FFT) analysis on incoming audio signals to identify frequency components characteristic of musical beats and rhythm sections. The embodiment incorporates onset detection algorithms that analyze spectral flux and energy variations in the audio signal to precisely identify the timing of musical beats and percussive events.

The embodiment provides light synchronization protocols wherein detected beat timing information triggers pre-programmed light patterns stored in non-volatile memory within the device. An exemplary embodiment includes beat-to-light mapping algorithms that translate detected BPM values into corresponding flash rates, with options for 1:1 beat matching, half-time patterns, and double-time patterns based on user preferences.

An embodiment incorporates adaptive synchronization logic that automatically adjusts light pattern timing based on beat prediction algorithms that anticipate upcoming beats based on established tempo patterns. The exemplary embodiment includes phase-locked loop circuitry that maintains precise synchronization between detected audio beats and light output timing, with compensation for processing delays to ensure visual-audio alignment.

In an exemplary embodiment, the system provides multiple beat synchronization modes including bass-reactive mode that responds primarily to low-frequency drum and bass elements, full-spectrum mode that reacts to all musical elements, and percussion-only mode that specifically targets drum beats and percussive instruments. The embodiment includes sensitivity adjustment controls accessible through tap gesture sequences that enable users to customize beat detection thresholds for different musical styles and volume levels. An embodiment incorporates anti-false trigger mechanisms including minimum beat interval timers and signal validation algorithms that prevent erroneous light activation from non-musical vibrations such as movement, handling, or environmental noise. An exemplary embodiment includes adaptive filtering that learns to distinguish between intentional musical input and incidental vibrations through pattern recognition algorithms.

The embodiment provides inter-device communication protocols for paired operation between left and right earplugs. An advanced embodiment includes external RF control capabilities for integration with venue lighting systems.

An embodiment of the invention provides one-to-many control protocols enabling a single mobile device to manage multiple earplug pairs simultaneously. The exemplary embodiment includes device identification and pairing systems that allow the mobile application to recognize, connect with, and coordinate lighting effects across multiple sets of earplugs within communication range.

In an exemplary embodiment, the system incorporates hierarchical control structures wherein one user can control lighting settings for an entire group of wearers, creating synchronized visual experiences across multiple participants. The embodiment provides group synchronization algorithms that ensure coordinated lighting patterns across all connected earplug devices, enabling unified visual displays for groups attending events together.

The preferred embodiment includes lithium battery specifications and placement within the compact housing design. An exemplary embodiment incorporates charging contacts and case interface design for seamless power transfer.

The embodiment includes power consumption optimization features for extended use periods. In an exemplary embodiment, the USB-C charging case configuration provides sufficient capacity for multiple charging cycles.

An alternate embodiment includes a rechargeable power source wherein the device 10 may include a case 200 for receiving a pair of earplugs 10 within the case 200 including a second power source 201 for charging the power source 103 of individual earplug devices. The embodiment may include charging elements 202 to couple with earplugs 10 at an exterior of the housing 100.

An exemplary embodiment includes mode indicators and user feedback systems integrated into the housing design. In the exemplary embodiment, tap gesture recognition enables intuitive control through the integrated tap sensor system. The embodiment includes charging procedures and status indication through visual feedback from the lighting elements. An embodiment includes a switch 104 coupled to the power source 103 for user-directed operation of the light source 120.

An exemplary embodiment incorporates capacitive touch sensing technology within the tap sensor system, wherein the tap sensor comprises a capacitive sensing electrode positioned beneath the exterior surface of the housing at the second end 102. The embodiment includes touch detection circuitry that monitors changes in capacitance when a user's finger contacts the exterior housing surface, enabling reliable detection of tap gestures even through the housing material.

In an exemplary embodiment, the tap sensor system includes gesture pattern recognition algorithms that distinguish between different types of user inputs including single taps, double taps, and long press gestures. The embodiment provides single tap functionality that cycles through predetermined color modes including red, blue, green, and white static color displays. An embodiment includes double tap activation that switches the device between static color mode and music-reactive "beat synch" mode.

Embodiments of the invention comprise manufacturing and packaging systems comprising EVA accessories that provide protective padding and organization for the complete system components. The EVA accessories include cable management solutions, protective foam inserts, and modular packaging components that ensure product protection during shipping and storage. The embodiment includes six sponge earplugs and six PET earplugs as alternative tip options, providing users with multiple fitting choices for optimal comfort and acoustic performance across different ear canal configurations.

An embodiment incorporates user interface enhancements through NFC card sticker technology that enables quick device pairing and setup through near-field communication protocols. The NFC functionality simplifies initial device configuration and enables rapid connection establishment between mobile devices and the earplug system. Additional packaging components include decorative stickers, comprehensive instruction manual, and specialized packaging box designed for retail presentation and product protection throughout the distribution chain.

The embodiment incorporates long press gesture detection wherein maintaining contact with the exterior housing (i.e. for longer than 2 seconds) activates brightness adjustment mode. In the exemplary embodiment, continued pressure during brightness adjustment mode enables users to cycle through multiple intensity levels ranging from 10% to 100% of maximum LED output.

An exemplary embodiment includes haptic feedback mechanisms within the housing structure that provide tactile confirmation of successful tap detection. The embodiment incorporates a micro-vibration motor positioned adjacent to the tap sensor that generates brief tactile pulses lasting approximately 50 milliseconds to confirm user input registration.

In an embodiment of the invention, the tap sensor system includes debouncing circuitry that prevents false triggering from accidental contact or environmental vibrations. The exemplary embodiment incorporates pressure threshold algorithms that require a minimum contact pressure equivalent to 20 grams of force to register as a valid tap gesture.

The embodiment provides mode state memory functionality wherein the device remembers the last selected lighting mode and brightness setting when powered off and restored upon reactivation. An exemplary embodiment includes power management protocols that automatically disable tap sensor functionality during charging cycles to prevent accidental mode changes while the device is connected to the charging case.

An embodiment incorporates visual feedback confirmation through the lighting elements wherein each successful tap gesture triggers a brief flash sequence lasting 200 milliseconds in the currently selected color to confirm mode changes. The exemplary embodiment provides error indication lighting that displays a red flash pattern when invalid or unrecognized tap sequences are detected.

In an exemplary embodiment, the exterior housing surface includes tactile reference marks positioned adjacent to the tap sensor area to enable users to locate the active touch region in low-light conditions. The embodiment incorporates raised surface texturing or recessed indicators that provide physical guidance for optimal finger placement during tap gesture operation.

Alternative embodiments include variations in acoustic filter materials and configurations, including different quartz formulations and positioning arrangements. Other embodiments provide different light element arrangements utilizing various colors and LED configurations.

Embodiments of the invention include multiple power source options, ranging from disposable batteries such as Zinc-air or AG2 sized alkaline or lithium-based batteries to rechargeable configurations. Alternative embodiments feature various housing materials and transparency levels to optimize light transmission characteristics.

Additional embodiments include alternative sensor configurations and placements for optimized vibration detection and tap sensitivity. Embodiments may incorporate additional electronic components including speakers, receivers, transmitters, communicators, and other components used in headphones for audio playback from connected devices.

Exemplary embodiments are specifically designed for gatherings, for example EDM and concert venue applications, where coordinated visual displays enhance the entertainment experience. The embodiment enables centralized lighting control systems for coordinated displays across multiple users. An embodiment provides venue-specific programming and customization options through RF connectivity. The embodiment includes safety considerations for high-volume environments while maintaining hearing protection.

Embodiments of the invention address component integration within compact housing designs while maintaining functionality of all electrical and acoustic systems. The embodiments include quality control measures for both acoustic and electronic performance validation. Exemplary embodiments utilize materials selection optimized for durability and user safety while maintaining the aesthetic and functional requirements. The embodiments consider production scalability and cost optimization for commercial manufacturing.

In embodiments of the invention, the housing 100 includes various electronic components such as the power source 103, switch 104, and circuitry to facilitate operation. These embodiments demonstrate the integration of traditional earplug functionality with advanced smart technology features for enhanced user experience.

An exemplary embodiment incorporates a centralized control system comprising a main controller unit positioned at a central location within an entertainment venue for coordinated management of multiple earplug devices. In this embodiment, the main controller unit is configured as a mixing console interface module that integrates with existing DJ equipment or concert sound mixing boards, enabling venue operators to synchronize lighting effects across all connected earplugs within the venue.

The embodiment includes a RF transmitter module positioned within the main controller unit, wherein the RF transmitter operates at predetermined frequency bands specifically allocated for venue-wide device communication. In an exemplary embodiment, the RF transmitter module comprises a high-power RF amplifier circuit capable of transmitting control signals across venue distances of up to 500 meters, ensuring reliable communication with all earplug devices within the entertainment space.

An embodiment of the invention provides automated control algorithms within the main controller unit that analyze real-time audio input signals from the venue's sound system to generate corresponding light pattern commands. The exemplary embodiment includes beat detection circuitry that processes audio frequencies in real-time to identify musical beats, bass drops, and rhythm patterns, automatically translating these audio characteristics into synchronized lighting commands transmitted to all connected earplugs.

In an exemplary embodiment, the main controller unit incorporates manual override controls including individual zone selection switches, intensity adjustment sliders, and pattern selection rotary encoders that enable a human operator to manually control lighting effects across different sections of the venue. The embodiment provides preset memory banks storing a variety of different lighting programs that can be instantly recalled and applied to all connected earplugs through simple button activation.

An embodiment includes RF receiver circuitry within each earplug device, wherein the RF receiver comprises a dedicated antenna element integrated into the housing structure and a signal processing module that decodes incoming control commands from the centralized controller. The exemplary embodiment incorporates frequency hopping protocols to prevent interference from other electronic devices within the venue environment while maintaining reliable communication links.

The embodiment provides venue mapping capabilities through zone designation protocols that enable the centralized controller to selectively address different groups of earplugs based on their physical location within the venue. In an exemplary embodiment, the system includes proximity detection sensors within the main controller unit that automatically identify and register new earplug devices entering the venue's RF coverage area.

An exemplary embodiment incorporates power management protocols within the centralized control system, wherein the main controller unit monitors battery levels of connected earplugs and adjusts lighting intensity commands to optimize power consumption across all devices. The embodiment includes low-power standby modes that maintain RF connectivity while minimizing power drain when lighting effects are not actively required.

In an embodiment of the invention, the centralized controller includes emergency override functionality that enables immediate shutdown of all lighting effects across connected earplugs through activation of a master emergency stop switch positioned on the main controller unit. The exemplary embodiment provides backup communication protocols that ensure continued operation of essential venue lighting coordination even in the event of primary RF system failures.

An exemplary embodiment incorporates professional venue integration capabilities through DMX protocol implementation for direct connection with professional lighting consoles. The embodiment includes DMX interface circuitry within the centralized RF controller that enables seamless integration with existing venue lighting control systems.

In an embodiment of the invention, the centralized controller incorporates MIDI interface capabilities for connection with DJ performance controllers and professional audio equipment. The exemplary embodiment includes MIDI-to-RF conversion modules that translate incoming MIDI control signals into corresponding RF commands for transmission to connected earplug devices.

The embodiment provides real-time show synchronization protocols that enable direct integration with venue lighting consoles and DJ equipment for coordinated audio-visual performances. An exemplary embodiment includes professional signal processing capabilities that interface with standard entertainment industry control protocols, allowing earplug lighting effects to be incorporated into comprehensive venue lighting designs.

In an exemplary embodiment, the system incorporates full-scale show integration algorithms that enable the earplug lighting system to participate as an integral component of professional entertainment productions. The embodiment provides scalable audience engagement features that transform individual earplug devices into elements of larger coordinated lighting displays spanning entire venue audiences While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An earplug device for noise suppression and entertainment lighting, comprising:
a housing generally being tubular in shape and comprising a first end and a second end opposite the first end;
a removable tip portion at the first end configured for receipt within an ear canal of a wearer;
a light element positioned at the second end and visible from an exterior of the housing when the device is worn;
an acoustic filter positioned adjacent to the first end within the housing;
a vibration sensor positioned within the housing and configured to detect musical beats in a frequency range of 20 Hz to 250 Hz;
a wireless communication module configured for inter-device synchronization and mobile device connectivity; and
a power source coupled to the light element and positioned within the housing.

2. The earplug device of claim 1, wherein the wireless communication module comprises a Bluetooth module configured to synchronize lighting effects between paired earplug devices and communicate with external mobile devices.

3. The earplug device of claim 1, wherein the vibration sensor comprises a piezoelectric accelerometer with signal conditioning circuitry configured to detect rhythmic patterns characteristic of musical beats.

4. The earplug device of claim 1, further comprising beat detection algorithms configured to calculate beats-per-minute in real-time and translate detected beats into corresponding light patterns.

5. The earplug device of claim 1, wherein the light element is configured to operate in multiple modes including static color mode, music-reactive mode, and synchronized group mode.

6. The earplug device of claim 1, further comprising a tap sensor integrated into an exterior surface of the housing and configured to detect user input gestures for mode switching.

7. The earplug device of claim 6, wherein the tap sensor comprises a capacitive sensing electrode configured to distinguish between single taps, double taps, and long press gestures.

8. The earplug device of claim 1, wherein the power source comprises a lithium battery, and further comprising a rechargeable charging case with Universal Serial Bus Type-C (USB-C) connectivity.

9. A smart earplug system for entertainment venues with centralized control, comprising:
a plurality of earplug devices, each earplug device comprising:
a tubular housing with a first end having a removable tip portion and a second end having a light element;

a quartz acoustic filter positioned within the housing adjacent to the first end;
a vibration sensor configured to detect low-frequency audio signals;
a wireless communication module configured for multi-device connectivity;
a centralized radio frequency (RF) controller configured to coordinate lighting effects across the plurality of earplug devices within an entertainment venue; and
professional venue integration protocols including Digital Multiplex (DMX) and Musical Instrument Digital Interface (MIDI) interface capabilities.

10. The smart earplug system of claim 9, wherein the centralized RF controller comprises a mixing console interface module configured to integrate with disc jockey (DJ) equipment and professional lighting consoles.

11. The smart earplug system of claim 9, wherein the system includes DMX-to-RF conversion modules for translating professional lighting control signals into RF commands.

12. The smart earplug system of claim 9, further comprising one-to-many control protocols enabling a single mobile device to manage multiple earplug pairs simultaneously.

13. The smart earplug system of claim 9, wherein the system provides group synchronization algorithms for coordinated lighting patterns across multiple users.

14. An earplug device with mobile application control, comprising:
a housing generally tubular in shape with a first end configured for ear canal insertion and a second end with a visible light element;
an acoustic filter positioned within the housing adjacent to the first end, wherein the acoustic filter comprises a quartz material configured to maintain sound wave stability;
a Bluetooth communication module configured to interface with another earplug to synchronize the lighting with the other earplug;
a microprocessor configured to receive control commands from the mobile application and adjust light element operation accordingly; and
a rechargeable power source positioned within the housing.

15. The earplug device of claim 14, wherein the smartphone application provides real-time control capabilities for immediate lighting adjustments.

16. The earplug device of claim 14, wherein the system enables hierarchical control structures where one user can control lighting for an entire group of wearers.

17. The earplug device of claim 14, further comprising group formation and management protocols for coordinated visual experiences.

18. The earplug device of claim 14, wherein the acoustic filter is positioned in communication with a pathway through an aperture in the second end of the housing.

19. A method of operating a smart earplug system with mobile application control, comprising:
inserting earplug devices into ear canals, each earplug device having a quartz acoustic filter and a controllable light element;
establishing wireless communication between the earplug devices;
detecting musical beats using vibration sensors within the earplug devices;
receiving control commands from the mobile application for lighting mode adjustments;

synchronizing light patterns across multiple earplug devices using group coordination protocols; and integrating with professional venue systems via Digital Multiplex (DMX) and Musical Instrument Digital Interface (MIDI) connectivity.

20. The method of claim 19, further comprising managing multiple sets of earplugs simultaneously through a single mobile device interface.

21. The method of claim 19, further comprising coordinating lighting effects with professional venue lighting systems through centralized RF control.

22. The method of claim 19, further comprising detecting user input gestures through tap sensors and switching between static color mode and music-reactive mode based on the detected gestures.

23. The method of claim 19, further comprising automatically adjusting light pattern timing based on beat prediction algorithms that anticipate upcoming beats.

24. The method of claim 19, further comprising providing venue-wide synchronization of light pulses across all connected earplug devices.

25. The method of claim 19, further comprising translating detected beats-per-minute (BPM) values into corresponding flash rates with options for beat matching, half-time patterns, and double-time patterns.

* * * * *